United States Patent
Cialdi et al.

(10) Patent No.: US 6,339,074 B1
(45) Date of Patent: *Jan. 15, 2002

(54) SULFATED HYALURONIC ACID AND ESTERS THEREOF

(75) Inventors: Gloria Cialdi, deceased, late of Siena, by Rolando Barbucci, legal representative; Agnese Magnani, San Rocco A. Pilli, both of (IT)

(73) Assignee: Fidia Advanced Biopolymers, Srl, Brindisi (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/447,429

(22) Filed: Nov. 23, 1999

Related U.S. Application Data

(62) Division of application No. 09/126,135, filed on Jul. 30, 1998, now Pat. No. 6,051,701, which is a division of application No. 08/553,290, filed on Feb. 8, 1996, now Pat. No. 6,027,741.

(30) Foreign Application Priority Data

Mar. 23, 1994 (IT) .......................................... PD9400054
Mar. 23, 1995 (WO) .............................. PCT/EP95/01111

(51) Int. Cl.$^7$ ............................................. A61K 31/715
(52) U.S. Cl. ............................. 514/54; 514/56; 514/59; 424/442; 424/493; 536/18.7; 536/21; 536/53; 536/123.1; 536/124
(58) Field of Search ................................. 424/442, 443; 514/54, 56, 59; 536/18.7, 21, 53, 123.1, 124

(56) References Cited

U.S. PATENT DOCUMENTS

| | | | |
|---|---|---|---|
| 2,599,172 A | 6/1952 | Hadidian et al. | 536/55.1 |
| 4,141,746 A | 2/1978 | Schweiger et al. | 106/168.01 |
| 5,013,724 A | 5/1991 | Petitou et al. | 514/54 |
| 5,017,229 A * | 5/1991 | Burns et al. | 106/162 |
| 5,202,431 A | 4/1993 | Della Valle et al. | 536/55.1 |
| 5,442,053 A | 8/1995 | Dalla Valle et al. | 536/55.1 |
| 5,550,189 A * | 8/1996 | Qin et al. | 525/54.3 |
| 6,027,741 A | 2/2000 | Cialdi et al. | 424/422 |
| 6,051,701 A | 4/2000 | Cialdi et al. | 536/123 |

FOREIGN PATENT DOCUMENTS

| | | |
|---|---|---|
| EP | 0011322 | 5/1980 |
| EP | 0285357 | 10/1988 |
| EP | 0340628 * | 11/1989 |
| EP | 0464759 * | 1/1992 |
| EP | 0473564 | 3/1992 |
| EP | 0507604 * | 10/1992 |
| EP | 0582330 | 3/1994 |
| FR | 2584728 | 1/1987 |
| JP | 1279042 * | 10/1999 |
| WO | 8404453 | 11/1984 |
| WO | 8800211 | 1/1988 |
| WO | 8807060 | 9/1988 |
| WO | 8907932 | 9/1989 |
| WO | 9220349 | 11/1992 |
| WO | 9303776 | 3/1993 |
| WO | 9624392 * | 8/1996 |
| WO | 9720564 * | 6/1997 |
| WO | 9737002 * | 10/1997 |
| WO | 9811141 * | 3/1998 |
| WO | 9845334 * | 10/1998 |
| WO | 0054762 * | 9/2000 |

OTHER PUBLICATIONS

Windholz et al., *The Merck Index*, Ninth Edition, Merck & Co., Rahway, NJ, 1976, entry No. 4510 at pp. 607–608.

Karamanos et al., "Insolation and Chemical Study of the Glycoaminoglycans for Squid Cornea," *International J. Biochemistry*, 23(1), 67–72 (1991).

Allessandri et al., "Mobilization of Capillary Endothelium in Vitro Induced by Effectors of Angiogenesis in Vivo," *Cancer Research* 43, 1790–1797 (Apr. 1983).

Budavari et al., *The Merck Index*, Twelfth Edition, Merck & Co., Rahway, NJ, 1996, entry No. 4793 at pp. 813–814.

Ebert et al., "Heparin/Polymers for the Prevention of Surface Thrombosis," Chapter 4 in *Medical Application of Controlled Release*, vol. 2 (Applications and Evaluation), Langer et al. (eds.), CRC Press, Inc., Boca Raton, FL, 1984, pp. 77–106.

Uryu, "Artificial Polysaccharides and Their Biological Activities," *Progress in Polymer Science*, 18, 717–761 (1983).

Casu et al., "Biologically Active, Heparin Sulfate–Like Species by Combined Chemical and Enzymatic Modification of the *Escherichia coli* Polysaccharide K5," *Carbohydrate Letters*, 1, 107–114 (1994).

Barbucci et al., "Sulfated Hyaluronic Acid as Heparin–Like Material: Physiochemical and Biological Characterization," *J. Materials Science: Materials in Medicine*, 5, 830–833 (1994).

Ofosu, "Antithrombotic Mechanisms of Heparin and Related Compounds," Chapter 20 in *Heparin—Chemical and Biological Properties, Clinical Applications*, Lane et al. (eds), Edward Arnold (publ), London, England, 1989, pp. 433–449.

Nagasawa et al, "Chemical Sulfation of Preparations of Chondroitin 4–and 6–Sulfate, and Dermatan Sulfate. Preparation of Chondroitin Sulfate E–Like Materials from Chondroitin 4–Sulfate," *Carbohydrate Research*, 158, 183–190 (1986).*

(List continued on next page.)

Primary Examiner—Gary Geist
Assistant Examiner—L. Eric Crane
(74) Attorney, Agent, or Firm—Birch, Stewart, Kolasch & Birch, LLP

(57) ABSTRACT

Hyaluronic acid, hyaluronate esters and salts thereof are sulfated such that the number of sulfate groups per monomeric unit is in the range of from 0.5 to 3.5. The sulfated derivatives exhibit anticoagulant and cell adhesion reduction properties, and may be used to prepare biomaterials.

6 Claims, 5 Drawing Sheets

OTHER PUBLICATIONS

Search Report for PCT/EP95/01111, Jun. 22, 1995.*
Ito, Y., "Micropattern Immobilization of Polysaccharide," *Journal of Inorganic Biochemistry,* 79(1–4), 77–81 (Apr. 7, 2000).*
Barbucci et al., "Immobilisation of Sulphated Hyaluronan for Improved Biocompatibility," *Journal of Inorganic Biochemistry,* 79(1–4), 119–125 (Apr. 7, 2000).*
Naggi et al., "'Supersulfated' Heparin Fragments, a New Type of Low–Molecular Weight Heparin," *Biochemical Pharmacology,* 36(12), 1895–1900 (Jun. 15, 1987).*

* cited by examiner

SULFATED HYALURONIC ACID AND ESTERS THEREOF

BACKGROUND OF THE INVENTION

This application is a divisional of copending application Ser. No. 09/126,135, filed on Jul. 30, 1998 now U.S. Pat. No. 6,051,701, which is a Divisional Application of application Ser. No. 08/553,290 filed on Feb. 8, 1996, now U.S. Pat. No. 6,027,241 the entire contents of which are hereby incorporated by reference.

FIELD OF THE INVENTION

The present invention relates to the homogeneous sulfation of polysaccharides and semisynthetic derivatives thereof, in particular glycosaminoglycans such as hyaluronic acid and its esters and tetraalkylammonium salts, for the preparation of new biomaterials useful in biomedical, health care, and pharmaceutical applications, and to such biomateriale per se. Such sulfated derivatives exhibit antithrombotic activity as evidenced by the lengthening of both the thrombin time and the whole blood clotting time. Moreover, the absence of hemolysis and the growth and shape of endothelial cells placed in contact with such sulfated derivatives indicate that these materials are promising heparin-like compounds.

DESCRIPTION OF THE RELATED ART

Many molecules of biological origin are polyelectrolytes, and their interactions are very important in a wide variety of biochemical reactions. Consequently, synthetic and/or semisynthetic polyelectrolytes have been in use for some time now. These polyelectrolytes mimic the biological characteristics of natural polyelectrolytes, and can have somewhat different characteristics compared to the starting material.

Polyelectrolytes of biological origin include sulfated polysaccharides, and in particular, heparin and its derivatives (D. A. Lane and U. Lindahl, Eds., *Heparin-Chemical and Biological Properties, Clinical Applications*, Edward Arnold, London), which play an important role in cell-substrate interactions, particularly in the process of viral activity inhibition, in the process of blood coagulation, in lipid removal, etc.

Heparin is the most biologically reactive member of the family of sulfated glycosaminoglycans. It is well known for its antithrombotic and anticoagulant properties. In fact, it is extensively used in the management of cardiovascular diseases anti contributes enormously to the success of open heart surgery. Nevertheless, the structure of heparin is not simple and, due to the number of variations, is not entirely known. Commercial heparins consist of a spectrum of 21 heparins (Nader et al. (1974) *Biochem. Biophys. Res. Commun.* 57:488) ranging in molecular weights from 3,000 to 37,500 in varying anticoagulant activities.

The blood anticoagulant activity of heparin is attributed to structural features, e.g., degree of sulfation, degree of dissociation, particular sequences of $COO^-$ and $SO^-_3$ groups, as well as to molecular shape and size. These factors appear to be related to biological activity by virtue of their importance in the ion binding capacity of heparin (Stivala et al. (1967) *Arch. Biochem. Biophys.* 122:40). By virtue of its highly negatively charged nature, heparin has a strong affinity for cations, and its activity is pH-dependent.

Most of the readily available natural polysaccharides have been sulfated in an attempt to obtain heparin analogues (Hoffman et al. (982) *Carbohydrate Res.* 2:115; Kindness et al. (1980) *Brit. J. Pharmac.* 63:675; Horton et al. (1973) *Carbohydrate Res.* 30:349; Okada et al. (1979) *Makromol. Chem.* 180:813; Kikuchi et al. (1979) *Nippon Kagaku Kaishi* 1:127; Manzac et al. (1981) *Proc. Third M.I.S.A.O.* 5:504), and recently, sulfate, carboxylic, and sulfonate groups were attached to synthetic polymers such as polystyrene (Kanmaugue et al. (1985) *Biomaterials* 6:297) and polyurethane (Ito et al. (1992) *Biomaterials* 13:131). The anticoagulant activities of these materials were much lower than that heparin, and were dependent on the type and binding of the substituents, the degree of substitution, and sequences.

Some chemical reactions are known which make it possible to sulfate polysaccharides (WO 88/00211; EP 0 340 628; Nagasawa et al. (1986) *Carbohydrate Research* 158:183–190), but it has not yet been possible to obtain sulfated polysaccharides which, besides the chemical and chemical-physical characteristics peculiar to such polysaccharides, also possess new characteristics, such as anticoagulant activity.

SUMMARY OF THE INVENTION

The present approach to studying the structural properties associated with the anticoagulant properties of polysaccharides was first to choose polymers possessing well-defined chemical groups consisting of regular repeating units, and secondly to modify their chemical structure.

Such molecules must therefore:

(1) Contain regular sequences of monomeric units, and
(2) Be chemically modifiable without destroying their structure.

Hyaluronic acid, the major component of the mammalian extracellular matrix, consists of alternating units of N-acetylglucosamine and glucuronic acid residues, and therefore seems a suitable macromolecule.

The sulfation of alcoholic hydroxyls present in the polymeric chain of a polysaccharide or of one of its semisynthetic derivatives by the use of a suitable sulfating agent can lead to the formation of new derivatives with chemical-physical characteristics, but most of all biological characteristics, which are different from those of the starting material.

The polyelectrolyte polyssaccharides which can be used as substrates in the present invention include glycosaminoglycans. First and foremost among these is hyaluronic acid and the semisynthetic derivatives thereof. Some particularly important semisynthetic derivatives of hyaluronic acid are esters thereof with alcohols of the aliphatic, araliphatic, heterocyclic and cycloaliphatic series, designated "HYAFF," that are described in U.S. Pat. Nos. 4,851, 521, 4,965,353, and 5,202,431, and EP 0 216 453. Sulfation of such pre-processed biomaterials is a novel feature of the present invention. In this case, the sulfation reaction no longer occurs in the homogeneous phase, but rather on the surface of the biomaterial in the heterogeneous phase, activating the exposed hydroxyl groups toward the reaction solvent.

The degree of sulfation that can be obtained directly on the biomaterial is an important characteristic, and requires careful kinetic control. To avoid the solubilization of the biomaterial, induced by the increased hydrophilic nature of the polymer which constitutes the matrix, the number of $—SO_3$ groups per dimeric unit must not exceed a certain level, generally less than 1.5–2, depending upon the degree of hydrophilicity of the starting biomaterial. For example, in the case of HYAFF 11 films, wherein all the carboxyls are involved in ester bonding with benzyl groups, the maximum degree of sulfation should not exceed 1.5.

The reagents commonly used for sulfation include the complex between sulfur trioxide and pyridine ($SO_3$-pyridine).

The reaction is conducted by adding the sulfating reagent to a tetrabutylammonium salt of a polysaccharide in solution, or to a solution of a polysaccharide ester, which, in the case of partial esters, contains the remaining carboxy functions in the form of tetrabutylammonium salts, in aprotic solvents such as dimethylsulfoxide, N,N'-dimethylformamide, and N-methylpyrrolidone in the temperature range of from about 0° C. to about 60° C.

Different degrees of Bulfation, measured by the number of sulfate groups per disaccharide unit, are obtained by varying the quantity of $SO_3$-pyridine. The ratio between moles of hydroxyls and moles of sulfating reagent can vary between 1:1 and 1:12.

Surprisingly, the present inventors succeeded in sulfating the polysaccharide chain of hyiluronic acid and its semisynthetic derivatives in a specific and homogeneous manner without causing loss of the polymer's characteristics, in particular its molecular weight, thus obtaining new polymers with biological and physico-chemical characteristics which hyaluronic acid and its semisynthetic derivatives did not previously possess.

By this method, it is possible to obtain new polymers with different levels of sulfation, but with the same molecular weight. Polymers with new biological characteristics can be obtained by using as starting materials biopolymers wherein the carboxy groups are salified with tetrabutylammonium salt. Such biopolymrs are not hemolytic.

A notable characteristic of these sulfated polysaccharides is their ability to increase blood coagulation time. The thrombin time test is performed by measuring how long it takes for fibrinogen to turn to fibrin once thrombin has been added to a sample of human blood in the presence of the test material. The thrombin time test in the same blood sample, but in the presence of the polymer used as starting material, is taken as a reference value. The test loses significance at over 240 seconds. The coagulation time is determined by simply measuring the time taken for a sample of human blood to coagulate in the presence of the test material. Times exceeding two hours are not considered.

Using the new biopolymers of the present invention, it is possible to develop new biomaterials for use in the biomedical, health-care, and pharmaceutical fields. The products obtained possess biocompatible and biological characteristics such as antithrombotic, anticoagulant, and antiviral activities. For example, sulfated polyanions have been shown to exhibit antiviral activity, including HIV inhibition. The new biopolymers of the present invention can also be used to advantage in cell growth processes, in controlled drug release systems, and more generally, in internal surgery, in extracorporeal oxygen circulation, in adhesion prevention, in permanent and biodegradable implants, and in dialysis.

For example, as in the case of other sulfated polymers, such as dextrans, sulfated hyaluronic acid having a molecular weight in the range of between about 10,000 and about 50,000 Daltons inhibits the production of tumor necrosis factor (TNF), which is the main target in the proliferation of inflammatory cells. Sulfated hyaluronic acid can therefore be used as a local anti-inflammatory agent in the form of hyaluroric acid-based biomaterials or compositions.

The new polymers can therefore be prepared in the form of gels, creams, or ointments, and can be used to produce biomaterials in the form of threads, sponges, gauzes, membranes, guide channels, non-woven fabrics and microspheres, according to the therapeutic uses for which they are intended. Lastly, depending upon the degree of sulfation and the molecular weight of the polymer, it is possible to produce polymers exhibiting antiviral activity and/or which can be use to intervene in the various stages of cell interactions. These biopolymers can also be used in coating processes, lending new biological properties to the surface of support material such as biomedical objects and devices.

Such sulfated biomaterials can be employed in applications where the product comes into contact with the blood or highly vascularized tissues, e.g., the use of biopolymeric dialysis tubes or membranes for internal or external surgery, which are capable of reducing cell adhesion, etc. In particular, the new, soluble sulfated hyaluronic acid derivatives of the present invention can be employed in the wide variety of applications already well known in the art for hyaluronic acid-based biomaterials.

For example, while hyaluronic acid derivatives having a degree of sulfation greater than 2.5 exhibit good anticoagulant activity, the molecular weight of the starting polymer can also be significant in influencing the properties of the new sulfated biopolymers of the present invention.

In particular, at least four sulfated hyaluronic acid derivatives are notable due to their molecular weight and degree of sulfation. These are:

1. Hyaluronic acid having a molecular weight in the range between about 10,000 and about 50,000 Daltons, and having a degree of sulfation of 2.5, 30, or 3.5;
2. Hyaluronic acid having a molecular weight in the range between about 50,000 and about 250,000 Daltons, and having a degree of sulfation of 2.5, 3.0, or 3.5;
3. Hyaluronic acid having a molecular weight in the range between about 250,000 and about 750,000 Daltons, and having a degree of sulfation of 2.5, 3.0, or 3.5; and
4. Hyaluronic acid having a molecular weight in the range between about 750,000 and about 1,250,000 Daltons, and having a degree of sulfation of 2.5, 3.0, or 3.5.

The hyaluronic acid fractions having the molecular weights described above can be obtained by the use of membranes with particular molecular weight cut-off points, as is known in the art.

Among the semisynthetic ester derivatives of hyaluronic acid, polymeric matrices of HYAFF 11 (100% benzyl ester of hyaluronic acid) sulfated to degrees of 1.0 and 1.5, and HYAFF 11p75 (75% benzyl ester cf hyaluronic acid) sulfated to degrees of 0.5 and 1.0, are particularly interesting.

Further scope of the applicability of the present invention will become apparent from the detailed description and drawings provided below. However, it should be understood that the detailed description and specific examples, while indicating preferred embodiments of the present invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and which are not limitative of the present invention, in which:

FIGS. 4A and 4B show the preferential migration of endothelial cells towards Cu(II)-sulfated hyaluronic acid rather than towards sulfated hyaluronic acid alone. FIGs. 5A and 5B show the preferential migration of endothelial cells towards Cu(II)-heparin rather than towards heparin alone. FIGS. 6A and 6B show that there is no preferential migration of endothelial cells towards the Cu(II)-Tris complex rather than towards the medium alone.

DETAILED DESCRIPTION OF THE INVENTION

Figure 1:
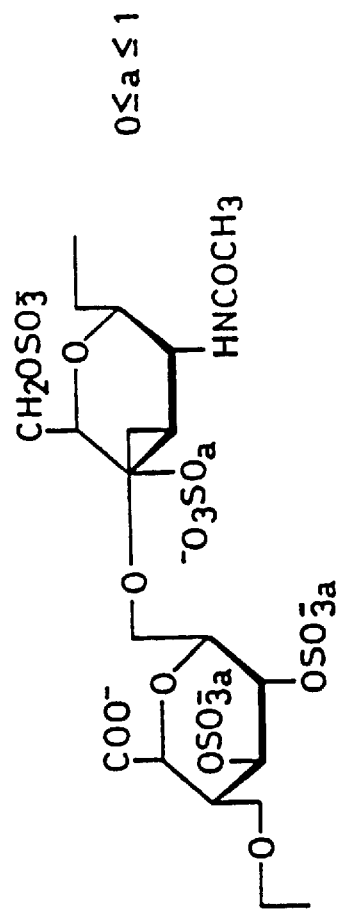
FIG. 1 shows the effect of hyaluronic acid sulfated with 2.0, 2.5, 3.0, and 3.5 $SO_3$ groups per repetitive unit on whole blood clotting time (WBCT) and thrombin time (TT).

The following detailed description of the invention is provided to aid those skilled in the art in practicing the present invention. Even so, the following detailed description should not be construed to unduly limit the present invention, as modifications and variations in the embodiments discussed herein may be made by those of ordinary skill in the art without departing from the spirit or scope of the present inventive discovery.

The contents of each of the references cited herein are herein incorporated by reference in their entirety.

Presented below for illustrative purposes are some examples of the preparation of new sulfated polymers according to the present invention. While these Examples are directed to hyaluronic acid and its semisynthetic derivatives such as tetrabutylammonium salts and esters, the same methods can be applied to other polysaccharides such as other glycosaminoglycans, alginic acid, gellan, carboxymethylcellulose, carboxy-methylamide, and carboxymethylchitin, and semisynthetic derivatives thereof, such as their tetrabutylammonium salts and partial esters with aliphatic, araliphatic, heterocyclic and cycloaliphatic alcohols, as described in U.S. Pat. Nos. 4,851,521, 5,122,598, 5,300,493, 5,332,809, and 5,336,668; European Patent Application No. 93917681.4; EP 0 216 453, EP 0 251 905, EP 0 342 557, EP 0 518 710, EP 0 603 264, and EP 0 605 478; and WO 93/06136 and WO 94/03499.

EXAMPLE 1

Sulfation of Sodium Hyaluronate, Sulfation Degree 3

0.250 grams of the tetrabutylammonium salt of hyaluronic acid are solubilized in 10 ml of dimethylformamide (DMF). 1.305 grams of $SO_3$-pyridine solubilized in 10 ml of DMF are added to this solution under a flow of nitrogen. The solution is shaken for an hour at a temperature of between 4° C. and 0° C. About 200 ml of purified water, chilled to 0° C., are subsequently added. The pH of the mixture is brought to a value of between 8.5 and 9.5 by adding 1M sodium hydroxide. The derivative is then precipitated with 120 ml of ethyl alcohol. Sodium acetate is added to saturation, and the precipitate is left to deposit for between 1 and 24 hours at a temperature of between 0° C. and 4° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by nuclear magnetic resonance (NMR).

Thrombin time and coagulation time in this and the following examples were determined as described in WO 92/11294. The product thus obtained has a thrombin time of 42.2 compared to the 11.3 seconds of the starting polymer, and a coagulation time of over 2 hours compared to 28 minutes measured in the control blood.

EXAMPLE 2

Sulfation of Sodium Hyaluronate, Sulfation Degree 3.5

0.250 grams of the tetrabutylammonium salt of hyaluronic acid are solubilized in 10 ml of dimethylformamide (DMF). 2.088 grams of $SO_3$-pyridine solubilized in 10 ml of DMF are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by nuclear magnetic resonance (NMR).

The product thus obtained has an infinite thrombin time, compared to 11.3 seconds for the starting polymer.

EXAMPLE 3

Sulfation of the Partial Ethyl Ester of Hyaluronic Acid: 75% of the Carboxy Groups are in the Form of the Ethyl Ester, Sulfation Degree 3

0.250 grams of the tetrabutylammonium salt of the 75% partial ethyl ester of hyaluronic acid (HYAFF-7p75) are solubilized in 10 ml of dimethylformamide (DMF). 1.305 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

The product thus obtained has a thrombin time of 45 seconds, compared to 11.3 seconds for the starting polymer, and a coagulation time of over 2 hours compared, to 28 minutes for tho control blood.

EXAMPLE 4

Sulfation of the Partial Ethyl Ester of Hyaluronic Acid: 50% of the Carboxy Groups are in the Form of an Ethyl Ester, Sulfation Degree 2.5

0.250 grams of the tetrabutylammonium salt of the 50% partial ethyl ester of hyaluronic acid (HYAFF-7p50, 50% of the carboxy groups esterified with ethanol) are solubilized in 10 ml of dimethylformamide (DMF). 1.044 grams et $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

The product thus obtained has a thrombin time of 47 seconds, compared to 11.3 seconds for the starting polymer, and a coagulation time of over 2 hours, compared to 28 minutes for the control blood.

EXAMPLE 5

Sulfation of the Partial Ethyl Ester of Hyaluronic Acid: 25% of the Carboxy Groups are in the Form of an Ethyl Ester, Sulfation Degree 2

0.250 grams of the TBA salt of a partial ethyl ester of hyaluronic acid (HYAFF-7p25, 25% of the carboxy groups esterified with ethanol) are solubilized in 10 ml of dimethylformamide (DMF). 0.783 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

The product thus obtained has a thrombin time of 49 seconds, compared to 11.3 seconds for the starting polymer, and a coagulation time of over 2 hours, compared to 28 minutes for the control blood.

EXAMPLE 6

Sulfation of the Partial Benzyl Ester of Hyaluronic Acid: 75% of the Carboxy Groups are in the Form of a Benzyl Ester, Sulfation Degree 3.5

0.250 grams of the tetrabutylammonium salt of a partial ethyl ester of hyaluronic acid (HYAFF-11p75, 75% of the carboxy groups esterified with benzyl alcohol) are solubilized in 10 ml of dimethylformamide (DMF) 2.088 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation, and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfacion is determined by NMR.

The product thus obtained has a thrombin time of 44 seconds, compared to 11.3 seconds for the starting polymer, and a coagulation time of over 2 hours, compared to 28 minutes for the control blood.

EXAMPLE 7

Sulfation of the Partial Benzyl Ester of Hyaluronic Acid: 50% of the Carboxy Groups are in the Form of a benzyl ester, Sulfation Degree 3

0.250 grams of the tetrabutylammonium salt of a partial ethyl ester of hyaluronic acid (HYAFF-11p50, 50% of the carboxy groups esterified with benzyl alcohol) are solubilized in 10 ml of dimethylformamide (DMF) 1.305 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturation and the precipitate is left to deposit for between 1 and 24 hours at a temperature of between 4° C. and 0° C. The precipitate is separated by centrifugation, for example for 15 minutes at 1,500 rpm, solubilized in purified $H_2O$, and then dialyzed until all residue reagent and reaction products have been completely eliminated. The degree of sulfation is determined by NMR.

The product thus obtained has a thrombin time of 46 seconds, compared to 11.3 seconds for the starting polymer, and a coagulation time of over 2 hours, compared to 28 minutes for the control blood.

EXAMPLE 8

Sulfation of the Partial Benzyl Ester of Hyaluronic Acid: 25% of the Carboxy Groups are in the Form of a Benzyl Ester, Sulfation Degree 2

0.250 grams of the tetrabutylammonium salt of a partial ethyl ester of hyaluronic acid (HYAFF-11p25, 25% of the carboxy groups esterified with benzyl alcohol) are solubilized in 10 ml of dimethylformamide (DMF). 0.522 grams of $SO_3$-pyridine solubilized in 10 ml of dimethylsulfoxide (DMSO) are added to this solution under a flow of nitrogen. The solution is shaken for at least an hour at a temperature of between 4° C. and 0° C. About 200 ml of $H_2O$, chilled to 0° C., are subsequently added. The pH of the mixture is brought to a value of between 8.5 and 9.5 by adding 1M sodium hydroxide. The derivative is then precipitated with 120 ml of ethyl alcohol. Anhydrous sodium acetate is added to saturations and the precipitate is left to deposit for between 1 and 24 hours at a temperature of between 4° C. and 0° C. The precipitate is separated by centrifugation, for example for 15 minutes at 1,500 rpm, solubilized in purified H$_2$O, and then dialyzed until all residue reagent and reaction products have been completely eliminated. The degree of sulfation is determined by NMR.

The product thus obtained has a thrombin time of 48 seconds, compared to 11.3 seconds for the starting polymer, and a coagulation time of over 2 hours, compared to 28 minutes for the control blood.

EXAMPLE 9

Preparation of Films of HYAFF 11, Sulfation Degree 1.5

0.250 grams of a film of HYAFF 11 are immersed in a bath of 250 ml of a mixture of chloroform:dimethylformamide in a ratio of 1:1. 50 ml of a solution obtained by solubilizing 3.4 grams of a complex of pyridine-SO$_3$ in dimethylformamide are then added.

The reaction is allowed to proceed for 2 hours at ambient temperature, after which the film is removed and then immersed in a bath of distilled water (100 ml), and lastly in a solution of water:ethanol, 50:50. The film is then oven-dried for 48 hours at 55° C.

EXAMPLE 10

Preparation of films of HYAFF 11p75, Sulfation Degree 1

0.250 grams of a film of HYAFF 11p75 are immersed in abath of 250 ml of a mixture of chloroform:dimethylformamide in a ratio of 1:1. 50 ml of a solution obtained by solubilizing 2.3 grams of a complex of pyridine-SO$_3$ in dimethylformamide are then added.

The reaction is allowed to proceed for 2 hours at ambient temperature, after which the film is removed and then immersed in a bath of distilled water (about 100 ml), and lastly in a solution of water:ethanol, 50:50. The film is oven-dried for 48 hours at 55° C.

EXAMPLE 11

Biological Characterization of Soluble Sulfated Hyaluronic Acid and Hyaluronic Acid Esters Whole Blood Clotting Time in the Presence of Sulfated Hyaluronic Acid Having Different Degrees of Sulfation This test was performed on hyaluronic acid and sulfated hyaluronic acid using blood from a single donor. The control contained blood alone.

For each test, three test tubes each containing 5 ml of blood were prepared. The first constituted the blank, while in the second and third, 25 mg of hyaluronic acid and 25 mg of sulfated hyaluronic acid were solubilized, respectively.

The results are shown in FIG. 1, where it can be seen that hyaluronic acid having 3.0 and 3.5 SO$_3$ groups per repetitive unit resulted in whole blood clotting times (WBCT) of infinity. Clotting time for whole blood controls was approximately 15 minutes. Blood in the presence of hyaluronic acid clotted after 45 minutes.

Thrombin Time in the Presence of Sulfated Hyaluronic Acid Having Different Degrees of Sulfation The thrombin time for hyaluronic acid having different degrees of sulfation was determined using an Elvi 820 Digiclot (Logos S.p.A, Milan, Italy). This device has an incubation plate set at a temperature of 37° C., and accomodates 32 test tubes and four reagent vials, two of which can be magnetically stirred at 600 rpm. It contains two thermostatic measuring wells, fitted with a magnetic stirrer at 300 rpm, and a light-proof lid. A magnetic pipette with adaptable volumes (0.1–0.2 ml) for reagent distribution activates the device, which is stopped by even the slightest variations in optical density with regard to clot formation. Clotting is monitored photometrically. A ray of light from a lamp first passes through a 525 nm interference filter, and lastly a capacity cell. A photodiode measures the variations in optical density of the plasma on clot formation. A photometric signal processor stops the digital chronometer at the nearest tenth of a second. The throbmin time test is performed using the reagent "Trombina" (Boehringer Mannheim GmbH Diagnostica).

The test is carried out on all samples using plasma obtained by centrifugation of blood from several donors (plasma pool) which had previously been treated with an anticoagulant (1 ml of a solution of sodium citrate/9 ml of blood). Solutions were prepared at concentrations of 1 mg/ml of hyaluronic acid and sulfated hyaluranic acid in phosphate buffer solution.

As summarized in FIG. 1, hyaluronic acid having 2.5, 3.0, and 3.5 SO$_3$ groups per repetitive unit lengthens the thrombin time. Hyaluronic acid having 2.0 SO$_3$ groups per repetitive unit did not lengthen the thrombin time, i.e., the thrombin time equalled that in the control, thus indicating that this particular sulfated hyaluronic acid derivative does not have heparin-like anticoagulant activity. Thrombin time in the presence of hyaluronic acid is similar to that in the control.

Also shown in FIG. 1 is the quantity of heparin corresponding to 1 mg of sulfated hyaluronic acid product, determined by means of a calibration curve.

Tharombin Time in the Presence of Sulfated Hyaluronic Acid Eaters Having Different Decrees of Sulfation Thrombin time was also determined on plasma in which sulfated derivatives of hyaluronic acid is (hyaluronic acid molecular weight=200,000 Daltons) i.e., HYAFF 11 (100% benzyl ester of hyaluronic acid; sulfation degree 2.0), HYAFF 11p25 (25% benzyl ester of hyaluronic acid; sulfation degree 3.0), and HYAFF 11p75 (75% benzyl ester of hyaluronic acid; sulfation degree 3.5) had been solubilized.

In the case of sulfated HYAFF 11, the influence of the concentration thereof, and of thrombin, on TT was investigated.

The results for sulfated HYAFF 11 are shown in Table 1, where hyaluronic acid was used as a reference as it is soluble in plasma, and wherein thrombin concentration is in International Units (UI).

TABLE 1

THROMBIN TIME IN THE PRESENCE OF SULFATED HYAFF 11

| SOLUBLE MATERIAL | QUANTITY mg/ml | [] THROMBIN | THROMBIN TIME |
| --- | --- | --- | --- |
| Plasma | — | ≈6 | 13 sec |
| Sulfated HYAFF 11 | 8 | ≈6 | 1 min 25 sec |
| Hyaluronic acid | 8 | ≈6 | 30 sec |
| Sulfated HYAFF 11 | 8 | ≈0.6 | 3 min |
| Hyaluronic acid | 8 | ≈0.6 | 50 sec |
| Sulfated HYAFF 11 | 2 | ≈6 | 18 sec |
| Hyaluronic acid | 2 | ≈6 | 17 sec |

These results disclose a longer thrombin time for plasma in the presence of sulfated HYAFF 11 than in the presence of hyaluronic acid. The influence of the concentrations of hyaluronic acid, sulfated hyaluronic acid, and thrombin should be noted. Sulfated HYAFF 11 (8 mg/ml) significantly prolonged thrombin time when thrombin is employed at either 6 UI or 0.6 UI as compared to hyaluronic acid. Low quantities (2 mg/ml) of sulfated HYAFF 11 do not result in any significant variation in thrombin time.

Table 2 shows the results for sulfated HYAFF 11p25 and sulfated HYAFF 11p75 on thrombin time.

TABLE 2

THROMBIN TIME IN THE PRESENCE OF
SULFATED HYAFF 11p25 AND SULFATED HYAFF 11p75

| SOLUBLE MATERIAL | QUANTITY | THROMBIN TIME |
| --- | --- | --- |
| Plasma | — | 10.3 sec |
| HYAFF 11p75 $SO_3$ | 5 mg/ml | 12.4 sec |
| HYAFP 11p25 $SO_3$ | 1 mg/ml | 19.4 sec |

The data in Table 2 demonstrate that both sulfated HYAFF 11p25 and sulfated HYAFF 11p75 prolong thrombin time. The longer thrombin time for sulfated HYAFF 11p75 corresponds to about 0.15 UI/ml of heparin activity. The longer thrombin time for sulfated HYAFF 11p25 corresponds to about 0.25 UI/ml of heparin activity.

Reptilase Time

Reptilase is an enzyme found in the venom of *Bothrox atrops* that clots fibrinogen by splitting off its fibrinopeptide A.

Reptilase time is determined by dissolving sulfated hyaluronic acid or sulfated hyaluronic acid derivative in 1 ml of 0.1 M phosphate buffered saline, 0.3 ml of which is then added to 0.3 ml of human plasma. The reptilase time is determined by incubating the human plasma containing the sulfated hyaluronic acid or derivative at 37° C. for two minutes, then adding Reptilase Reactive (fraction of thrombin extracts from *Bothrox atrops* venom, Hemodiagnostica Diagnostica Stago, Boehringer Mannheim), and measuring the clotting time automatically (Elvi Digiclot 2 Coagulometer, Logos S.p.A., Milan, Italy).

Table 3 shows the effects of the sulfated HYAFF 11, the sulfated HYAFF 11p25, and the sulfated HYAFF 11p75 on reptilase time.

TABLE 3

REPTILASE TIME IN THE PRENSENCE OF
SULFATED HYAFF 11, SULFATED HYAFF 11p25, AND
SULFATED HYAFF 11p75

| SOLUBLE MATERIAL | QUANTITY | REPTILASE TIME |
| --- | --- | --- |
| Plasma | — | 15 sec |
| Sulfated HYAFF 11 | 8 mg/ml | 15 sec |
| HYAFF 11p75 $SO_3$ | 5 mg/ml | 15 sec |
| HYAFF 11p25 $SO_3$ | 1 mg/ml | 15 sec |

The data in Table 3 show that none of the sulfated hyaluronic acid derivatives had any significant effect on reptilase time.

EXAMPLE 12

Hemolysis Test

The hemolysis assay measures the direct interaction of substances with the plasma membrane of erythrocytes. 25 mg of sulfated hyaluronic acid were dissolved in 0.5 ml of sodium citrate. The assay tube was then filled with 5 ml of fresh human blood. The control contained whole citrated blood only. The hemolysis test was carried out as described in Albanese et al. (1994) *Biomaterials* 15:129.

The results obtained with sulfated hyaluronic acid show that this material does not exhibit any hemolytic activity.

EXAMPLE 13

Biological Characterization of Insoluble Sulfated Hyaluronic Acid Derivatives

Thrombin Time in the Presence of Insoluble Films of Sulfated Hyaluronic Acid Esters Having Different Degrees of Sulfation The thrombin time test was performed on rounds of insoluble films of sulfated hyaluronic acid esters used to line cuvettes, essentially as described in Example 11 for sulfated hyaluronic acid having different degrees of sulfation. 1.2 ml of plasma were added to each cuvette, which was then incubated together with the film rounds for 10 minutes. 0.2 ml of thrombin reagent was then added, and the clotting time was monitored. Molecular weight of hyaluronic acid and degree of sulfation of the esters were as in Example 11.

The results are shown in Table 4.

TABLE 4

THROMBIN TIMES OF HUMAN PLASMA
PLACED IN CONTACT WITH FILMS OF INSOLUBLE
SULFATED HYALURONIC ACID ESTERS

| INSOLUBLE MATERIAL | QUANTITY | [] THROMBIN | THROMBIN TIME |
| --- | --- | --- | --- |
| Plasma | — | ≈6 | 9.7 sec |
|  |  |  | 10.0 sec |
| HYAFF 11p75 $SO_3$ | 0.044 gr | ≈6 | 8.3 sec |
|  |  |  | 8.8 sec |
| HYAFF 11p75 | 0.044 gr | ≈6 | 11.0 sec |
|  |  |  | 10.9 sec |
| HYAFF 11p75 $SO_3$ | 0.031 gr | ≈5 | 18.7 sec |
|  |  |  | 20.9 sec |
| HYAFF 11p75 | 0.031 gr | ≈6 | 17.9 sec |
|  |  |  | 18.1 sec |
| HYAFF 11p75 $SO_3$ | 0.031 gr | ≈1.5 | 12.3 sec |
|  |  |  | 13.1 sec |
| HYAFF 11p75 | 0.031 gr | ≈1.5 | 12.6 sec |
|  |  |  | 11.0 sec |
| HYAFF 11 | 0.031 gr | ≈6 | 15.6 sec |
|  |  |  | 17.0 sec |

The data in Table 4 reveal no significant variations in the thrombin times of plasma placed in contact with films of sulfated hyaluronic acid esters.

EXAMPLE 14

Growth of Cultured Human Umbilical Vein Endothelial Cells in the Presence of Sulfated Hyaluroic Acid Human umbilical vein endothelial cells were isolated from umbilical cords by collagenase digestion following a standard protocol. The cells were maintained in a 5% $CO_2$ atmosphere at 37° C. in Medium 199 (GIBCO Laboratories) with 20% fetal calf serum, L-glutamine, and gentamicin.

The endothelial cells were identified as such by their polygonal morphology. For proliferation experiments, cells were used when cultures had reached confluence. Hyaluronic acid was dissolved in Medium 199 until a concentration of 5 mg/ml was obtained. The assay was planned in order to allow contact periods of 24, 48, and 72 hours between the material and the cells. Every 24 hours the medium was removed from the wells and sterile PBS solution was rinsed over the film to remove the unattached cells. The cells were analyzed with an inverted microscope (DIAPHOT TMD Nikon) and pictures taken with a Nikon camera. The cells were then detached with trypsin and counted in a Burker chamber. Trypan Blue was used to distinguish between dead and live cells.

Figure 2:
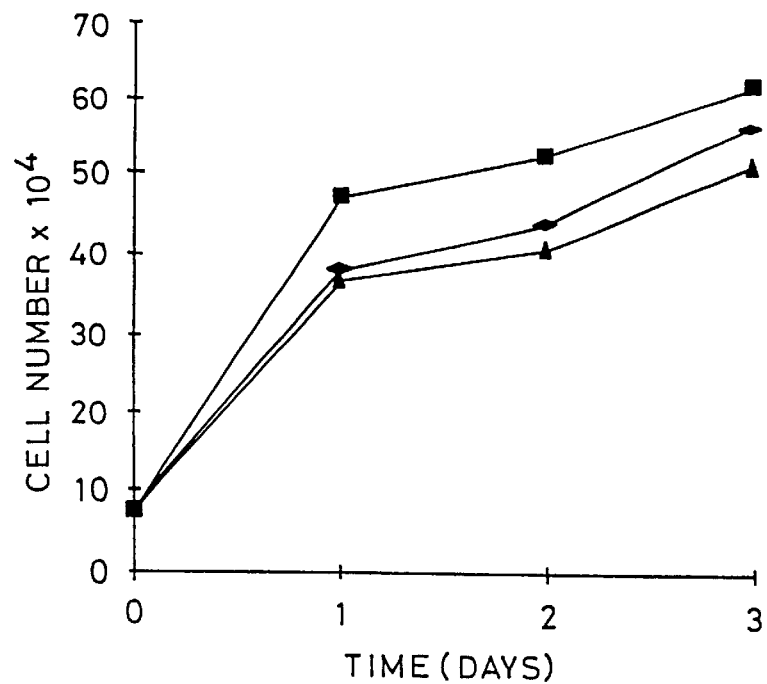
FIG. 2 shows the growth of human umbilical vein endothelial cells in control medium (♦), sulfated hyaluronic acid-containing medium (■), and hyaluronic acid-containing medium (▲) as described in Example 14.

FIG. 2 shows the human umbilical vein endothelial cells (HUVEC) growth curves.

The number of endothelial cells in medium containing sulfated hyaluronic acid increased with time, and better growth is shown than in medium containing hyaluronic acid or in a pure medium control.

The morphology of endothelial cells was examined using inverted microscopy. Endothelial cells in medium containing sulfated hyaluronic acid were well spread, with morphological alteration and without structural changes in cell organization.

The same morphology was noted for the endothelial cells in the presence of hyaluronic acid and for the control. The only remarkable difference was in the cell proliferation. In fact, after one day, the cells in the medium containing sulfated hyaluronic acid were almost a confluent monolayer, while the cells in medium containing hyaluronic acid or pure medium reached confluency only after three days.

EXAMPLE 15

Assessment of Induction of Angiogenesis In Vitro

Sulfated hyaluronic acid, like heparin, forms complexes with the Cu(II) ion, having a stoichiometric composition of $Cu(OH)_2L$ (L"="ligand") (Barbucci et al. (1995) *Gazetta Chimica Italiana*, in press). As is known from the literature, the Cu(II)-heparin complex exhibits an angiogenic effect (Alessandri et al. (1983) *Cancer Research* 43:1790–1797).

The ability of sulfated hyaluronic acid to induce angiogenesis in vitro using a cell migration method (Alessandri et al. (1983) *Cancer Research* 43:1790–1797) was therefore investigated.

Figure 3A:
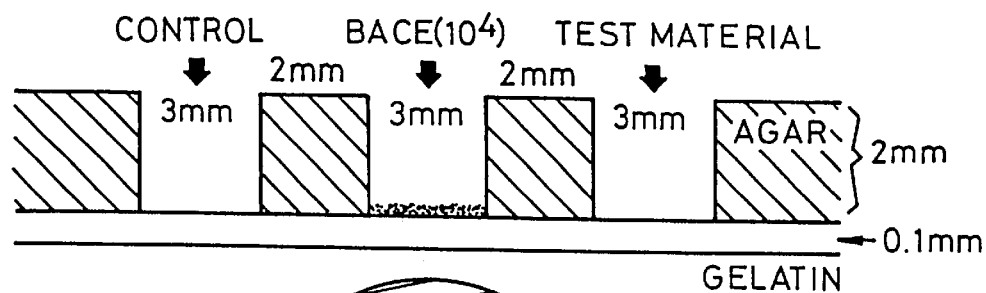
FIG. 3 is a schematic representation of a dish prepared for the gelatin-agarose test described in Example 15. Top: a cross-section showing a central well and two adjacent wells located 2 mm away. The BACE is placed in the central well, and the test material and the control are placed in the adjacent wells. Bottom: dish ready for the test. A fourth well containing BACE is placed about 2 cm away from the three aligned wells (proportions of distances not maintained in the figure). The fourth well is far removed from the influence of the is test material, and is utilized as a control to assure that the migration of BACE outside the well occurs as a uniform halo when no treatment is applied.
Figure 3B:
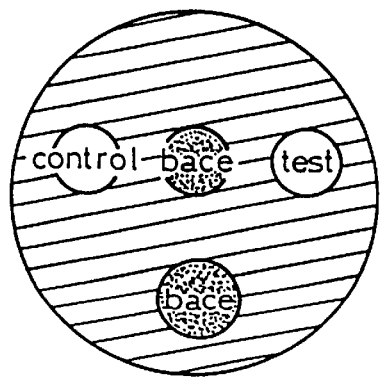

The migration of endothelial cells in agar was observed, the method being schematically shown in FIG. 3. The ability of a test sample to induce angiogenesis in vitro can be determined by the number of endothelial cells that preferentially migrate towards the test sample rather than towards the control sample.

The cell migration test to assess angiogenesis induced by the complex Cu(II)-heparin, as described in Alessandri et al., was conducted in a buffer solution of 0.1 M Tris, pH 7.5. However, in the presence of Tris, the complex formed is actually Cu(II)-Tris, not Cu(II)-heparin, so that the angiogenic effect observed relates to the Cu(II)-Tris complex in the presence of heparin.

The present tests were conducted using a buffer solution of 0.1 M PBS, pH 7.4. At this pH, the Cu(II) that is not in the complex precipitates in the form of a hydroxide. Solutions of Cu(II)-biological molecule were therefore filtered on cellulose filters having a pore size of 0.2 microns in order to eliminate the copper hydroxide precipitate before using solutions for testing.

Two samples of sulfated hyaluronic acid, one with 2.0 $SO_3$ groups, and the other with 3.5 $SO_3$ groups, per repetitive unit were analyzed. Experiments were run in replicate, and samples containing the complexes CU(II)-heparin and Cu(II)-Tris were also analyzed. In each experiment, the angiogenic effect of the complex Cu(II)-biological molecule was assessed in comparison to that of the biological molecule alone. Specifically, Cu(II)-sulfated hyaluronic acid was compared to sulfated hyaluronic acid, and Cu(II)-hoparin was compared to heparin. In the case of Cu(II)-Tris, the control sample contained only medium.

As shown in FIGS. 4A, 4B, 5A, 5B, 6A, and 6E, the complex Cu(II)-sulfated hyaluronic acid (3.5 $SO_3$ groups per repetive unit) proved capable of inducing angiogenesis in vitro to an extent similar to that of the complex Cu(II)-heparin.

Figure 4A:
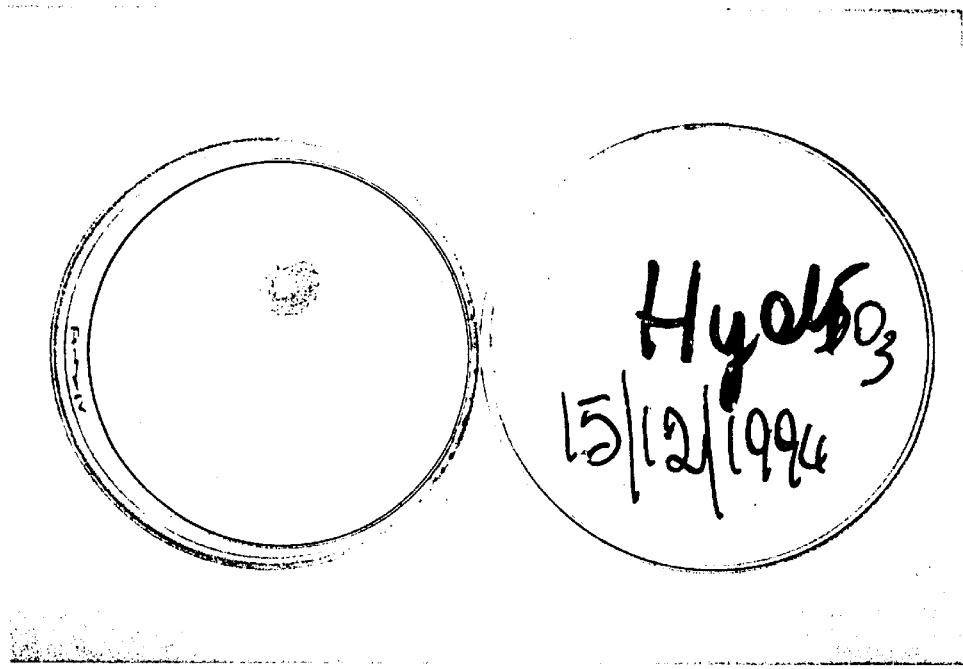
FIGS. 4A, 4B, 5A, 5B, 6A, and 6B illustrate the results of the assessment of induction of angiogenesis in vitro described in Example 15.
Figure 4B:
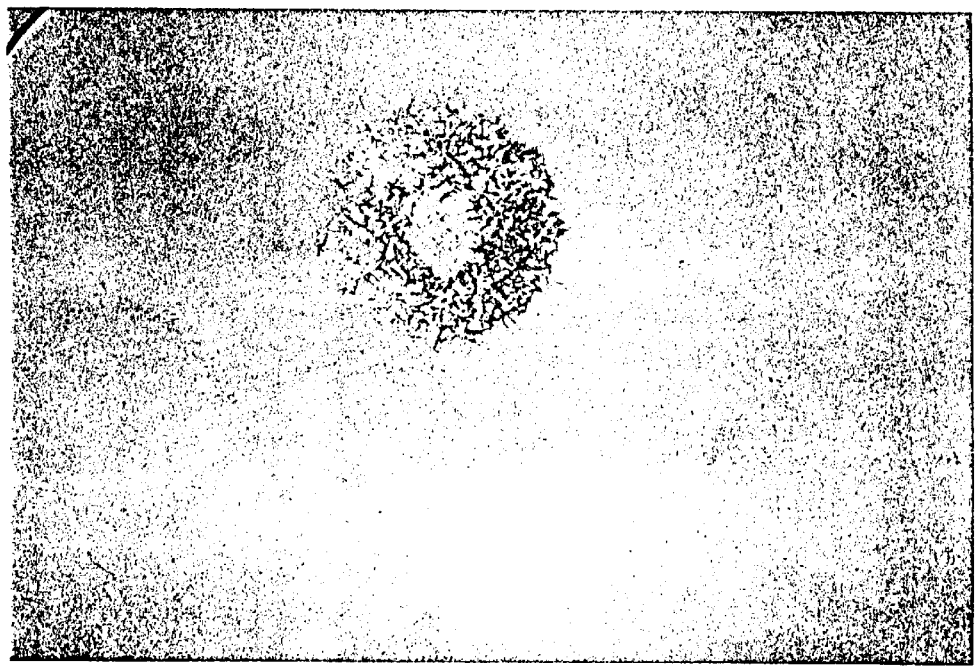

As shown in FIGS. 4A and 4B, there is a preferential migration by endothelial cells towards Cu(II)-sulfated hyaluronic acid rather than towards sulfated hyaluronic acid alone.

Figure 5A:
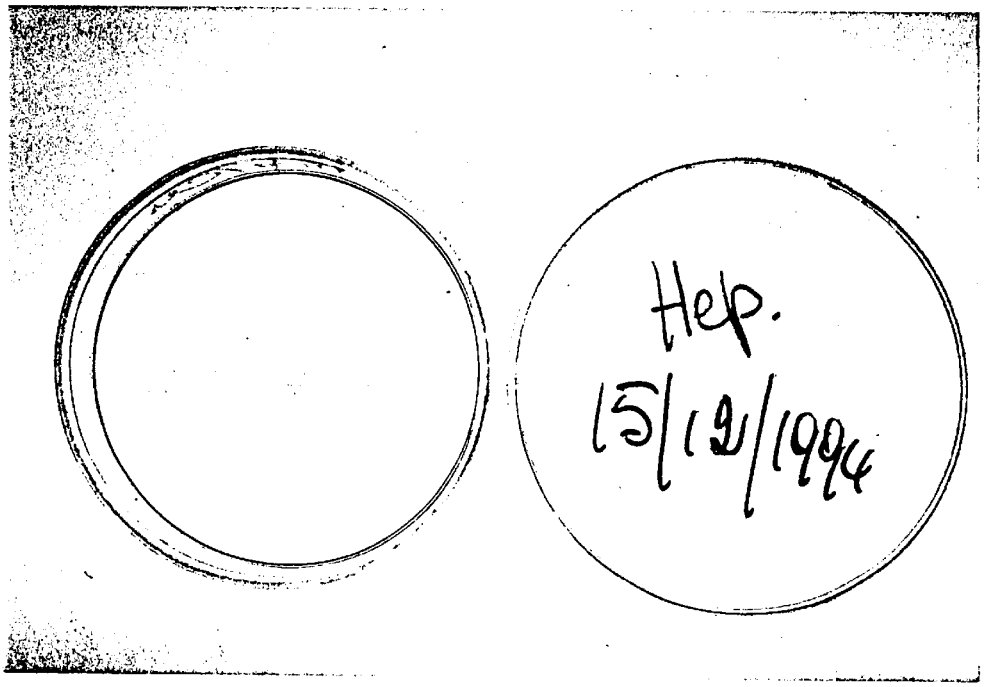
Figure 5B:
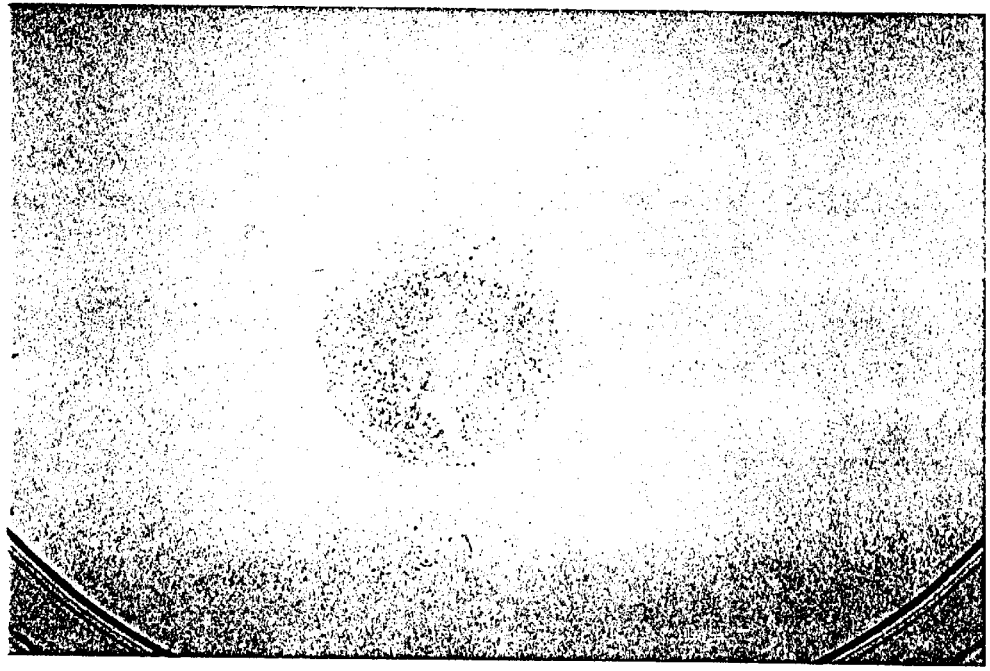

In the case of heparin, endothelial cells preferentially migrate towards the complex Cu(II)-heparin rather than towards heparin alone (FIGS. 5A and 5B).

The effect is more pronounced with sulfated hyaluronic acid than with heparin (compare FIGS. 4A, 5A and 4B, 5B).

Figure 6A:
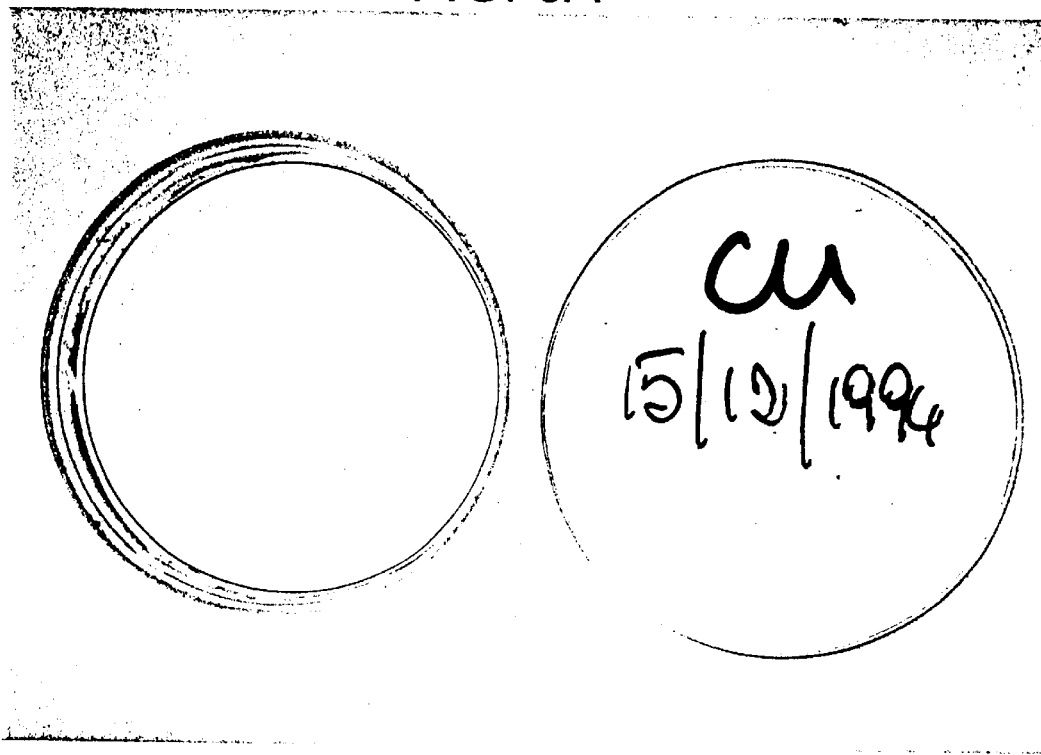
Figure 6B:
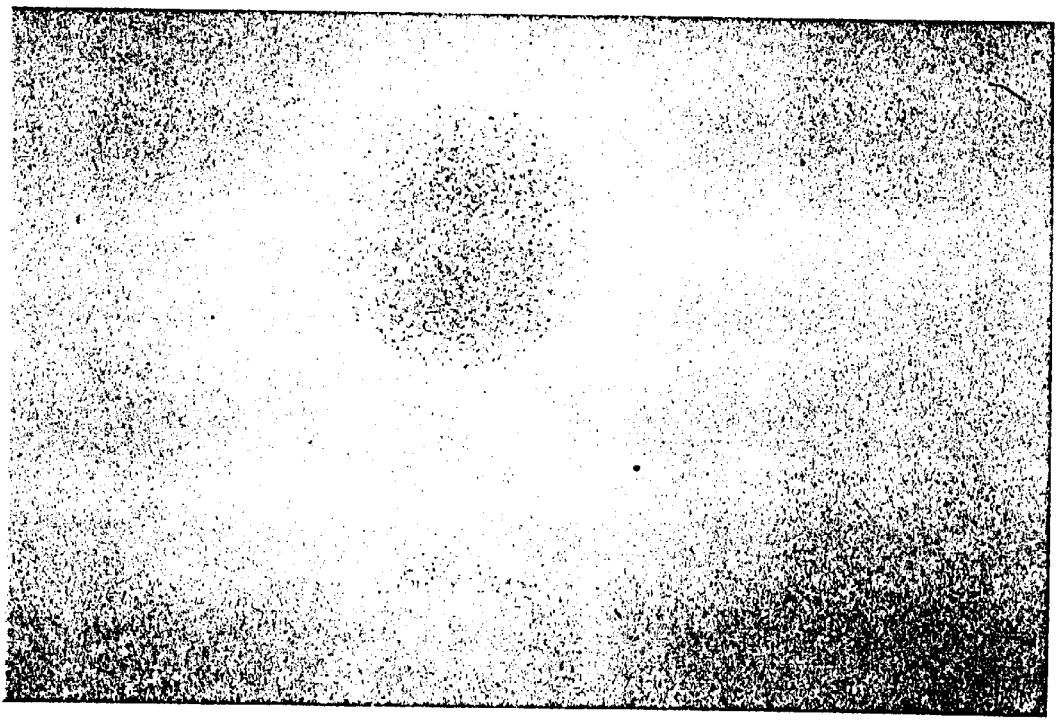

On the other hand, in the case of the complex Cu(II)-Tris (FIGS. 6A and 6B), there is no preferential migration of the cells towards the complex rather than towards the medium alone.

The effect of the sample containing Cu(II)-sulfated hyaluronic acid (2.0 $SO_3$ groups per repetitive unit) was comparable to that of the complex Cu(II)-Tris rather than to that of the complex Cu(II)-heparin. This demonstrates that the number of $SO_3$ groups per repetitive unit significantly influences obtaining heparin-like activity in inducing angiogenesis in vitro.

EXAMPLE 16

Pharmaceutical Compositions

Pharmaceutical preparations and biomaterials comprising the new sulfated derivatives of hyaluronic acid and other sulfated polysaccharides of the present invention can be administered to humans, alone or in association with other chemical polymers, such as polyurethane, polylactic acid, carboxymethylcellulose, carboxymethylchitin, carboxymethyl starch, and crosslinked polymers, or hyaluronic acid esters, salts, derivatives, complexes, fragments, subunits, and/or pharmacologically acceptable drugs, as aids in the biomedical, health care, and pharmaceutical fields.

Because of their antithrombotic and anticoagulant activities, the biopolymers of the present invention may be advantageously used to prepare biomaterials such as guide channels, bypasses, artificial veins, or shunts to be employed in hemodialysis, cardiology, extracorporeal circulation, and more generally, in the cardiovascular system.

The angiogenic activity of Cu(II)-sulfated hyaluronic acid complexes can be employed in stimulating capillary growth.

It has recently been demonstrated that sulfated hyaluronic acid is a potent inhibitor of Tumor Necrosis Factor-α (TNF-α) and TNF-β (Chang et al. (1994) *Journal of Leukocyte Biology* 55:778–784). Thus, the sulfated hyaluronic acid and hyaluronic acid ester products of the present invention can also find therapeutic use as anti-inflammatory agents in the treatment of TNF-mediated inflammation, systemic toxicity, and related pathologies.

Furthermore, sulfated hyaluronic acid derivatives can be employed as coatings for the surfaces of materials using techniques such as plasma coating to produce devices to be used in extracorporeal circulation applications.

The sulfated hyaluronic acid derivatives of the present invention can also be used in the form of gauzes, threads, gels, hydrogels, sponges, membranes, non-woven tissues, and microspheres, according to the therapeutic use for which they are intended, to promote cell growth processes, such as keratinocyte growth, to accelerate healing in patients affected by bedsores, wounds, burns, and skin ulcers, or as anti-adherents in surgery.

Depending upon the degree of sulfation and the molecular weight of the polymer, the new sulfated polysaccharides of the present invention can also be used alone or in association with other chemical polymers, such as those listed above, or with cross-linked polymers or hyaluronic acid esters, salts, derivatives, complexes, fragments, subunits, and/or pharmacologically acceptable drugs, for example in dermatology, ophthamology, otorhinolaryngology, odontology, gynecology, urology, and as drug delivery systems in the treatment of bacterial, mycotic, or viral infections.

Examples of combination medicaments according to the present invention include:

- association of sulfated hyaluronic acid and a hyaluronic acid ester, such as the benzyl or ethyl ester;
- association of sulfated hyaluronic acid and a crosslinked hyaluronic acid ester;
- association of sulfated hyaluronic acid and a chemical polymer such as that listed supra;
- association of sulfated hyaluronic acid and Cu(II) ions;
- association of sulfated hyaluronic acid and a metal ion, such as calcium or silver;
- association of sulfated hyaluronic acid and a hyaluronic acid ester, with an antiinfective agent such as a basic or non-basic antibiotic, sulfamidic, antiviral (such as acyclovir), steroid antiinflammatory (such as hydrocortisone or prednisolone), non-steroid antiinflammatory (such as indomethacin), a wound healer (such as epidermal growth factor), an antimicrobial, an antibacterial, or a disinfectant;
- association of sulfated hyaluronic acid and a crosslinked hyaluronic acid, with an antiinfective agent such as a basic or non-basic antibiotic, sulfamidic, antiviral (such as acyclovir), a steroid antiinflammatory (such as hydrocortisone or prednisolone), a non-steroid antiinflammatory (such as indomethacin), a wound healer (such as epidermal growth factor), an antimicrobial, an antibacterial, or a disinfectant.

The invention being thus described, it is obvious that the same can be modified in various ways. Such modifications are not to be considered as divergences from the spirit and scope of the invention, and all such modifications that would appear obvious to one skilled in the art are intended to come within the scope of the following claims.

What is claimed is:

1. A biomedical product comprising sulfated hyaluronic acid or a salt thereof; wherein the number of sulfate groups per disaccharide unit is in the range of from 0.5 to 3.5; wherein the molecular weight range of the hyaluronic acid or salt is between about 50,000 and about 1,250,000 Daltons; wherein the biomedical product is selected from the group consisting of a guide channel, a bypass, an artificial vein, a shunt, a gauze, a thread, a gel, a hydrogel, a film, a membrane, a sponge, a non-woven tissue, and a microsphere; and wherein the biomedical product is not a structure coated with the sulfated hyaluronic acid or salt.

2. A biomaterial for promoting cell growth processes which comprises sulfated hyaluronic acid or a salt thereof, wherein the number of sulfate groups per disaccharide unit is in the range of from 0.5 to 2.5, wherein the molecular weight range of the hyaluronic acid is between about 50,000 and about 1,250,000 Daltons, and wherein the biomaterial is not a structure coated with the sulfated hyaluronic acid or salt.

3. The biomedical product of claim 1, wherein the molecular weight of the sulfated hyaluronic acid or salt is between about 100,000 and 1,250,000 Daltons.

4. The biomedical product of claim 1, wherein the molecular weight of the sulfated hyaluronic acid or salt is between about 200,000 and 1,250,000 Daltons.

5. The biomaterial of claim 2, wherein the molecular weight of the sulfated hyaluronic acid or salt is between about 100,000 and 1,250,000 Daltons.

6. The biomaterial of claim 2, wherein the molecular weight of the sulfated hyaluronic acid or salt is between about 200,000 and 1,250,000 Daltons.

* * * * *